US007435350B2

(12) United States Patent
Noyes et al.

(10) Patent No.: US 7,435,350 B2
(45) Date of Patent: Oct. 14, 2008

(54) INTELLIGENT SYSTEM AND METHOD FOR AUTOMATED PACKING OF CHROMATOGRAPHY COLUMNS

(75) Inventors: Aaron Noyes, Cambridge, MA (US); Jeremy Perreault, Leominster, MA (US); Mark Carroll, Londonderry, NH (US)

(73) Assignee: Millipore Corporation, Billerica, MA (US)

( * ) Notice: Subject to any disclaimer, the term of this patent is extended or adjusted under 35 U.S.C. 154(b) by 684 days.

(21) Appl. No.: 11/098,505

(22) Filed: Apr. 4, 2005

(65) Prior Publication Data

US 2006/0219616 A1    Oct. 5, 2006

(51) Int. Cl.
*B01D 15/08* (2006.01)
(52) U.S. Cl. .................................... 210/656; 210/198.2
(58) Field of Classification Search ................. 210/635, 210/656, 659, 198.2; 95/82; 96/101; 422/70
See application file for complete search history.

(56) References Cited

U.S. PATENT DOCUMENTS

| 5,951,873 | A | 9/1999 | Shalon et al. ............... 210/656 |
| 6,843,918 | B2 | 1/2005 | Hauck et al. ................ 210/656 |
| 7,238,282 | B2 * | 7/2007 | Perreault et al. ......... 210/198.2 |
| 2004/0099604 | A1 | 5/2004 | Hauck et al. ................ 210/656 |
| 2007/0262021 | A1 * | 11/2007 | Perreault et al. ............ 210/656 |

OTHER PUBLICATIONS

The European Search Report dated Oct. 8, 2007.

Journal of Chromatography A, 762 (1997) 83-88; Georges Guiochon et al.; "Consolidation of particle beds and packing of chromatographic columns".

Journal of Chromatography A, 741 (1996) 175-184; "Consolidation of the packing material in chromatographic columns under dynamic axial compression IV. Mechanical Properties of some packing materials" Brett J. Stanley et al.

Journal of Chromatography A., 989 (2003) 79-94; Martin Hofmann; "Use of ultrasound to monitor the packing of large-scale columns, the monitoring of media compression and the passage of molecules, such as monoclonal antibodies, through the column bed during chromatography".

European Search Report dated Jul. 31, 2006.

Columns for Chromatography In Industrial Purification and Laboratory Use; Amicon a Grace company; Publication No. 531.

MicroPatent Search EP0008921; Column Chromatography and Like Processes and Apparatus for the Practice Thereof; Wright Scientific Limited.

(Continued)

*Primary Examiner*—Ernest G Therkorn
(74) *Attorney, Agent, or Firm*—Nields & Lemack (57) ABSTRACT

The present invention provides an automated system and method for packing chromatography columns. In one embodiment, the system first determines the type of media that is present in the column, and uses this information to generate an automated procedure to pack the specific media type. In a second embodiment, the media type is made known to the system, such as via input from the operator. The system then uses this information, in the same manner as in the first embodiment, to generate an automated procedure to pack the specific media type. Finally, in a third embodiment, parameters such as column height and rate of compression are made known to the system, such as via input from the operator. The system then packs the column in accordance with these supplied parameters.

10 Claims, 5 Drawing Sheets

OTHER PUBLICATIONS

Moduline Industrial Chromatography Column Operating Instructions; Publication No. Amicon a Grace company (cover page and last page The Moduline Industrial Chromatograph Column Operating Instructions consists of a cover page and a final page with Amicon contact information on it.

* cited by examiner

Constant Velocity Pack Algorithm

Figure 4

Constant Pressure Pack Algorithm

Figure 6

INTELLIGENT SYSTEM AND METHOD FOR AUTOMATED PACKING OF CHROMATOGRAPHY COLUMNS

BACKGROUND OF THE INVENTION

The present invention relates to chromatography columns and in particular to a chromatography column system and methods of packing a chromatography column. Frequently, it is desirable to separate out one or more useful components from a fluid mixture that contains other components that may not be useful or are less valuable. To accomplish this, it is often necessary or desirable to fractionate such a fluid mixture to separate out the useful or desired components. This can be carried out by using liquid chromatography systems. Liquid chromatography may be described as the fractionation of components of a mixture based on differences in the physical or chemical characteristics of the components. The various liquid chromatographic systems fractionate the components with a fractionation matrix. Some liquid chromatographic matrix systems fractionate the components of a mixture based upon such physical parameters as molecular weight. Still other liquid chromatographic systems will fractionate the components of a mixture based upon such chemical criteria as ionic charge, hydrophobicity, and the presence of certain chemical moieties such as antigenic determinants or lectin-binding sites on the components.

Chromatography systems of various sizes are used in both laboratory analysis operations and for industrial scale production operations in which separation steps such as separating out a fraction from human blood or separating out impurities from a pharmaceutical can be carried out on a large scale in a batch process.

Separations using chromatography columns filled with chromatographic media have been carried out for years. The chromatographic media typically comprises particles having a diameter between 5 and 100 µm. To maximize the effectiveness of the column, it is desirous to arrange the media as tightly and as uniformly as possible. This process, known as packing, eliminates voids and channels within the media. However, chromatography column packing, particularly where large columns are involved, is highly variable and can dramatically affect the efficiency of the separation. Many setup process parameters must be smoothly orchestrated in order to achieve a homogenous packed column. Depending on the size of the column, the packing process can take a significant amount of time, in the range of several hours. Yet despite the time invested in packing the column, often times less than 50% of these packed columns function in accordance with the specification. During chromatography packing and operation, the compaction of the chromatographic media has a significant impact on the performance and repeatability of the column. In packing the column, typically the media is compressed through an alternating process of flowing liquid through the column to pack the media and then lowering the adjuster assembly in an effort to mechanically compress the media.

Therefore, there is a need for an improved method of packing columns, which both reduces the time required and improves the repeatability and yield of the process. Improvements in column design can reduce operator packing error and lead to better performance, reproducibility and stability of chromatography beds, as can the incorporation of controlled means to automatically perform one or more of the processes involved in column packing.

SUMMARY OF THE INVENTION

The problems of the prior art have been overcome by the present invention, which provides an automated system and methods for packing chromatography columns. In one embodiment, the system first determines the type of media that is present in the column, and uses this information in conjunction with an automated procedure to pack the specific media type. In a second embodiment, the media type is made known to the system, such as via input from the operator. The system then uses this information, in the same manner as in the first embodiment, in conjunction with an automated procedure to pack the specific media type. Finally, in a third embodiment, parameters such as column height and rate of compression are made known to the system, such as via input from the operator. The system then packs the column in accordance with these supplied parameters.

DETAILED DESCRIPTION OF THE INVENTION

Currently, most chromatography columns are packed manually, which can be a long tedious procedure. Those workers who are packing the columns must be specially trained and require time and practice to improve their proficiency. Despite this, the yield of manually packed columns rarely exceeds 50%. Thus, more than half of the columns that are packed do not meet their requirements, thereby necessitating the need to pack them again. This results in inefficiency, and more specifically in the loss of time and media. Automation can be used to significantly improve the yield and reduce the time required to pack a column.

The present invention utilizes a chromatography column, used in conjunction with several additional components. The first such component is an actuator, which is capable of moving an adjustable bed support, or adjuster, located within the column. This actuator can be driven by any suitable means, such as a pneumatically, electrically or hydraulically driven means. This adjustable bed support can be moved by the actuator so as to increase or decrease the pressure exerted on the media bed. A second such component is means for measuring the total pressure or force exerted on the media bed. This can be implemented in many forms, such as a pressure sensor, a load cell or through the use of a calibrated hydraulic cylinder. One such implementation is described in co-pending application Ser. No. 11/072,081. The output generated by these means can be in a variety of forms, including but not limited to analog voltage, analog current, and digital signals. A third component is a means for measuring the pressure of the fluid entering the column. This can be implemented in many forms, such as a bubble trap or a pressure sensor. A fourth component is a controller capable of receiving these measurements from the pressure measuring devices and using these measurements to control the actuator. One skilled in the art will appreciate that the controller can be of various types, including, but not limited to proportional, proportional-derivative (PD), proportional integral (PI) or proportional-integral-derivative (PID), and that the invention is not limited by the choice of the controller. Similarly, the output from the controller to the actuator can be in various forms, including but not limited to analog voltage, current, digital signals, or pulses. A means for measuring the position of the adjustable bed support within the column is also provided. The position of the bed support can be measured using optical sensors, acoustical sensors, visually using a clear column such as one made of glass or plastic and preferably a marked gradient or scale applied to the wall surface or can be determined based on the actions of the actuator. For example, the position of the bed support can be determined based on the number of rotations made by a worm gear, or the number of pulses applied to a step motor.

Figure 1:
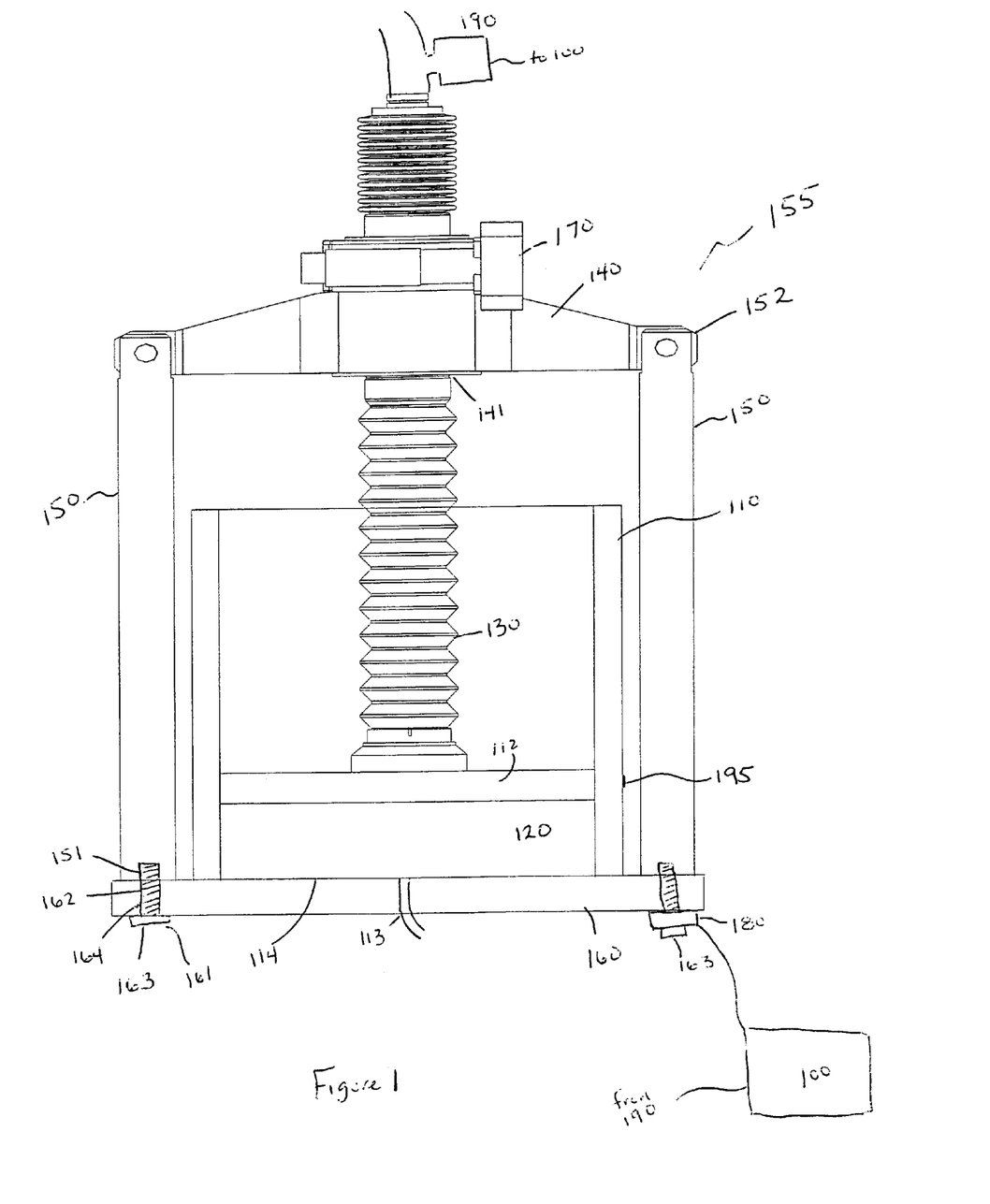
FIG. 1 illustrates the preferred embodiment of the present invention.

FIG. 1 illustrates the preferred embodiment of the present invention. Adjustable bed support 112 is coupled to a shaft 130, which is preferably threaded. Shaft 130 passes through an opening 141 in yoke 140, which opening is also preferably threaded. Yoke 140 is held in position by stanchions 150, which are mounted to a base 160, on which the column 110 preferably rests. In the preferred embodiment, the stanchions 150 are held in contact with the base through the use of fasteners 161, such as bolts, which extend through openings 164 in the base and engage with the stanchion via slots 151 bored into the stanchion, which are also threaded. The fastener has a shaft 162, which is preferably threaded, of a given diameter, and a head 163 having a diameter larger than that of the shaft. The openings 164 in the base 160 are preferably larger than the diameter of the fastener's shaft 162, but smaller than the diameter of the fastener's head 163, to allow the fastener's shaft to move freely through the opening 164. The fastener 161 is inserted from the underside of the base 160, through the opening 164 such that the fastener's shaft 162 engages with the slot 151 in the stanchion 150.

Yoke 140 is affixed to a plurality of stanchions 150. Two stanchions typically provide the needed structural stability for smaller diameter columns, while additional stanchions may be used for large diameter columns. These stanchions 150 are preferably placed equidistant from one another around the circumference of a circle that is concentric to, but larger than column 110. The stanchions 150 have a height equal to, or preferably greater than, that of the column 110.

In one embodiment, yoke 140 is connected to the two or more stanchions and it spans the width and centerline of the column 110. The yoke 140 is retained on the stanchions 150 by means such as slot 152, a ring or other device that can affirmatively hold the yoke 140 in place. The yoke 140 may be permanently attached to the stanchions 150 or more preferably, it may be removably connected to the stanchions 150 by bolts, clevis pins, cotter pins, clamps and the like. In one preferred embodiment, the yoke 140 is attached to one stanchion 150 by a bolt, and the other stanchion by a clevis pin so that when adjustable bed support 112 is withdrawn from the column, the yoke 140 can be pivoted vertically about stanchion 150 containing the bolt and moved up and out of the way of the column to allow easy access to the column interior.

Atop the yoke 140 is an actuator 170 adapted to move the shaft in the vertical direction, independent of the yoke 140. Suitable actuator drivers include pneumatic, electric or hydraulic drivers. In the preferred embodiment, a motor, preferably electrically powered, is equipped with a gear that contacts the threaded shaft 130. The movement of the motor causes the rotation of the gear, which in turn causes rotation of the threaded shaft 130. The resulting rotation of the threaded shaft 130, through the threaded opening 141 in yoke 140 causes the shaft 130 to move relative to the yoke 140 in the vertical direction.

The adjustable bed support 112, shaft 130, and actuator 170 comprise the adjuster assembly. These components operate in unison to adjust the position of the adjustable bed support 112 inside the column 110, thereby also controlling the pressure exerted on the media bed.

The yoke 140 and the stanchions 150 comprise a support structure 155. This structure is rigidly coupled and is affixed to the shaft 130 and the base 160, such that any force exerted on adjustable bed support 112 is transferred through shaft 130, through support structure 155, to the connection point between the support structure 155 and the base 160.

While this embodiment comprises a preferred embodiment in which a single shaft with 2 stanchions is used, the invention is not so limited. Those skilled in the art will appreciate that it is within the scope of the present invention to use multiple shafts and a greater number of stanchions. For example, a very large diameter column may require a greater number of shafts and stanchions in order to insure that the adjustable bed support descends uniformly and evenly onto the media bed.

In the preferred embodiment, a load cell 180 is located between the head 163 of the fastening device and the underside of base 160. However, the load cell 180 can be positioned in any location where it can measure the force exerted on the media bed. A load cell is a device that translates the load exerted on it into an analog electrical output, such as voltage or current, or a digital electrical output. The relationship between the exerted load and the electrical output is well established and tightly controlled, such that the exact load experienced by the load cell can be determined by monitoring its electrical output. The term load cell is used herein to include any device that carries out this function.

The load cell 180 is preferably circular, with a concentric opening in the middle, such that the diameter of the opening is large enough to allow shaft 162 to be slid through the opening. However, the diameter of the opening is preferably smaller than the diameter of the head 163 of the fastener, such that the head cannot pass through the opening, thereby causing the load cell to interconnect with the fastener in a similar manner as a traditional washer. Thus, the fastener is inserted through the concentric opening in the load cell 180, through the opening in the base 160, and into the slot of stanchion 150. Preferably, one load cell is used, regardless of the number of stanchions, however multiple load cells, or one load cell for each stanchion, are also envisioned as an embodiment of the present invention.

One skilled in the art will appreciate that although the preferred embodiment comprises an adjustable top bed support, and a fixed lower bed support, the invention is not so limited. The apparatus can also be constructed such that the top support is fixed, and the lower bed support is adjustable.

In the preferred embodiment, the fluid to be processed by the column 110 travels in a conduit through a hollow cavity within shaft 130 to adjustable bed support 112. Alternatively, the fluid may also travel in a conduit parallel to the shaft and then enter the adjustable bed support under a hollow arch formed at the base of the shaft. Adjustable bed support 112 also comprises a flow cell, which equally distributes the fluid such that it enters the media bed uniformly. The processed fluid then exits the column through bottom flow port 113.

Those skilled in the art will appreciate that the direction of the fluid's travel is not limited to top to bottom; the fluid can also be forced into the bottom of the column and drawn out of the top surface. Similarly, it is not required that the fluid entry and the movable support be located in the same end of the column.

The pressure of the fluid entering the column is monitored. There are a number of methods known in the art for performing this monitoring. For example, a bubble trap can be inserted between the source of the fluid and the entrance to the shaft 130. A pressure sensor associated with the bubble trap can be used to supply the measured fluid pressure. In the preferred embodiment, a pressure sensor 190, preferably a transducer, is in communication with the fluid flow through the use of a T connection in close proximity to the shaft 130. A pressure transducer is used to convert a pressure measurement into either an analog or digital electrical signal, such as voltage or current. In this scenario, the transducer 190 measures the pressure of the fluid being forced through the conduit and into the column 110.

Finally, means 195 for measuring the position of the adjustable bed support 112 within the column 110 is provided. This position can be measured indirectly by monitoring the activities of the actuator. Alternatively, the position of the adjustable bed support can be monitored through the use of various types of sensors.

Using the apparatus described above, each of the three embodiments of the invention will be described. In the first embodiment, the system first determines the type of media that is present in the column, and uses this information in conjunction with an automated procedure to pack the specific media type.

The media type is determined in accordance with the following algorithm. The column is filled with slurried media of an unknown type. The actuator then moves the adjuster, preferably an adjustable bed support 112, toward the media at a constant velocity. As the bed support 112 is moved, the force exerted on the adjustable bed support is measured, such as by load cell 180. The position of the upper bed support 112 within the column 110 is also measured, such as by optical sensors. The pressure applied by the adjustable bed support, calculated as the measured force divided by the surface area of the adjustable bed support, is then compared to the distance that the adjustable bed support has moved.

Figure 2:
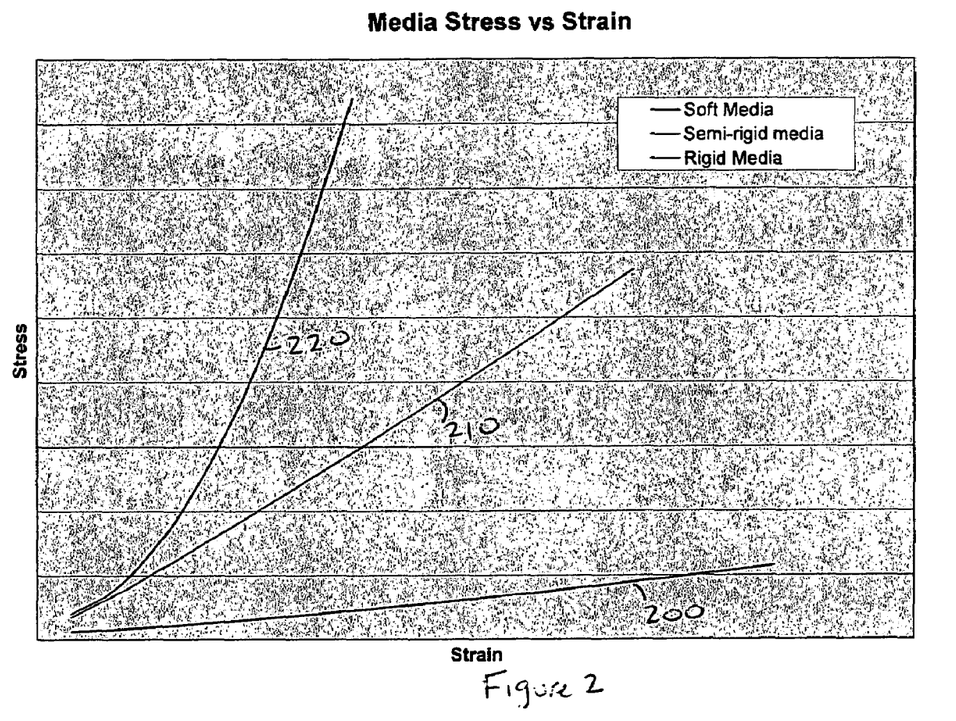
FIG. 2 represents a graph illustrating the relationship between stress and strain for various media types.

This relationship can be graphed as illustrated in FIG. 2. In this figure, the vertical axis, labeled "stress", is defined as:

$$\text{Stress} = \text{Force}_{measured} / \text{Area}_{adjustable\ bed\ support}$$

The horizontal axis, labeled "strain", is defined as:

$$\text{Strain} = \text{Column Height}_{start\ of\ process} / \text{Column Height}_{current}.$$

FIG. 2 illustrates the relative differences between various media types. Soft media 200 offers the lowest amount of resistance as the adjustable bed support moves toward it. Conversely, rigid media 220 offers a great amount of resistance as the adjustable bed support is moved toward it. Based on the resultant graph, the media type can be determined. Alternatively, each media type illustrated in FIG. 2 exhibits a near linear relationship between stress and strain. Therefore, rather than plotting a series of many successive points, it is possible to compute the slope of the resulting line by calculating the strain and stress at only two column heights. Alternatively still, since strain is defined as starting column height divided by current column height, the type of media can be determined by comparing the pressure exerted on the adjustable bed support to the current column height. Since the stress—strain graph is nearly linear, and current column height is inversely proportional to strain, the product of pressure and current column height is approximately a constant, for a given media type, if the starting column height and adjustable bed support area are fixed values. Once determined, this constant can be used to determine the type of media being used. Finally, the current column height is also related to the distance that the adjustable bed support 112 has moved. Therefore, in another embodiment, the movement of the adjustable bed support can be compared to the force (or pressure) applied to the bed support to determine the media type.

Once the media type has been determined, the column can be packed in accordance with the present invention. In the first embodiment, the system determines the media type as described above. In the second embodiment, the media type is made known to the system, such as by keyboard input. This input can be provided in a number of ways, including but not limited to selecting from a menu listing possible media types, and entering via a keypad or keyboard the name or a symbol associated with a media type.

Once entered, the system can pack the column in accordance with the present invention. Two methods of packing a chromatography column are described. The first embodiment moves the adjustable bed support 112 at a constant velocity and measures the resulting pressure exerted on the bed support. The second embodiment maintains the hydraulic pressure at a constant level and monitors the resulting velocity.

Figure 4:
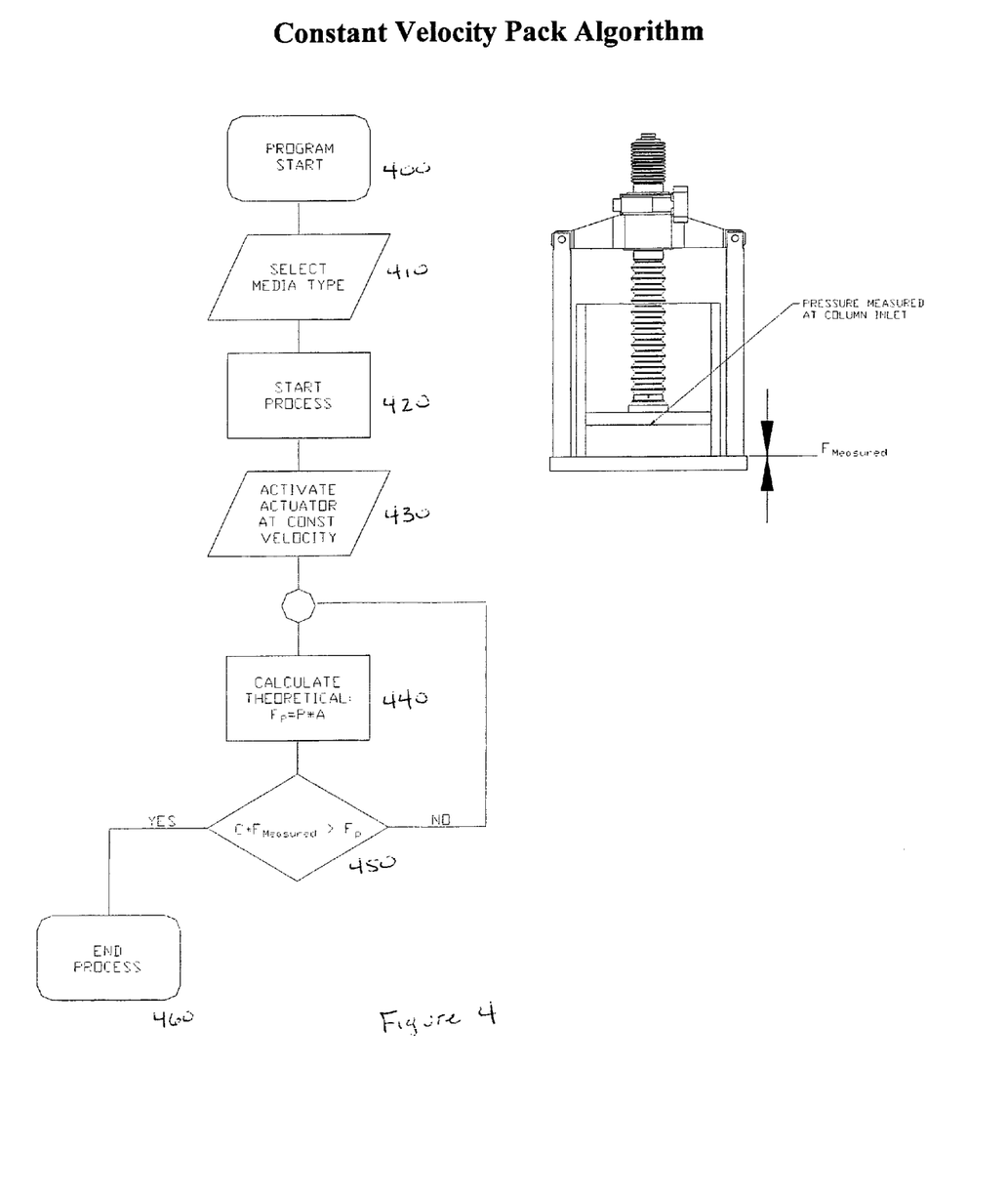
FIG. 4 represents a flowchart illustrating the steps performed during a constant velocity packing process in accordance with the present invention.

A flowchart showing one embodiment of a constant velocity packing process algorithm is illustrated in FIG. 4. In Block 410, the media type is made known to the algorithm. This determination can be performed empirically using the techniques previously described, or can be input to the system, such as via a keyboard or menu selection. The media type allows the controller to define a number of parameters which are needed by the algorithm, such as the velocity at which the adjustable bed support is to travel, and the sensitivity of the system (as described below). Once these parameters are established, the process begins. The system, namely the controller, activates the adjuster, preferably an adjustable bed support, moving it toward the media at a constant velocity as shown in Box 430. In Box 440, the column inlet force, which is the force exerted by the fluid entering the column, is measured. In the preferred embodiment, the measurement is performed by the pressure sensor 190 and the result is transmitted to the controller. In Decision Box 450, this inlet force, which is represented as the pressure reading from pressure sensor 190 multiplied by the area of the adjustable bed support, is compared to the force measured at the load cell 180.

Figure 3:
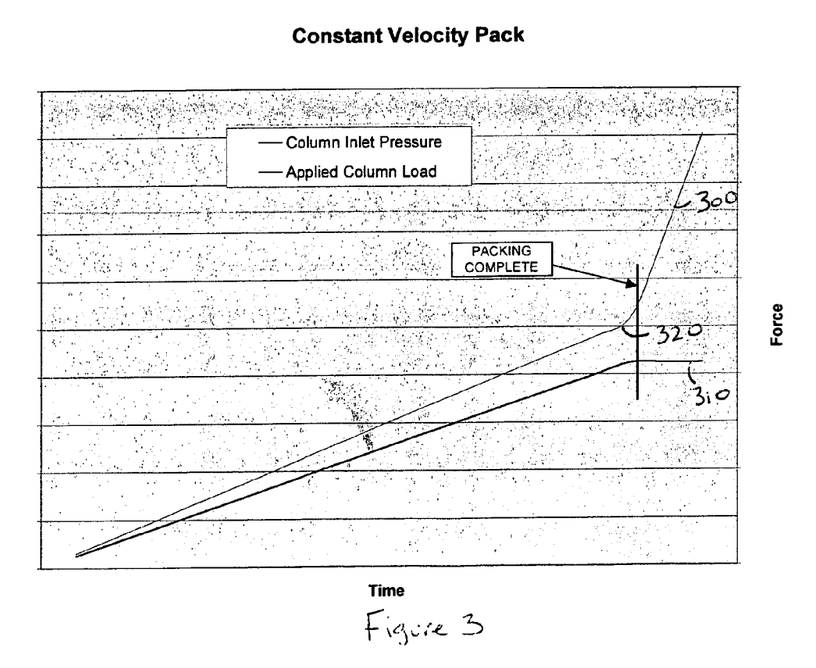
FIG. 3 represents a graph illustrating the forces during a constant velocity packing process in accordance with the present invention.

FIG. 3 is a graphical representation illustrating the forces being exerted on the adjustable bed support as a function of time. Line 300 represents the total force as measured by the load cell 180. This force includes the force of the media compression in addition to the hydraulic backpressure force. Line 310 represents the force related to the inlet pressure, which is the hydraulic backpressure force. Thus, the difference between these lines is the force caused by the media compression. As the packing process begins, the column inlet force 310 represents a significant part of the total force experienced by the load cell 180, as shown in line 300. This is due to the fact that the media is under little or no compression, thus this force is minimal. However, when the column becomes packed, the media compression force component begins to dominate the total force, causing line 300 to experience a large increase in slope. After this point in time, the inlet pressure becomes a much smaller percentage of the total force.

Decision Box 450 compares the inlet pressure to the total measured force. The variable C, shown in Box 450 indicates the desired ratio of the inlet force to the total force, and is a function of the media type. As long as the ratio of the inlet force to the total measured force is greater than the value of C, the controller will enable the adjustable bed support to continue traveling at its predetermined velocity. However, as soon as the inlet force drops below a targeted percentage of the total measured force, the process terminated in Box 460. For example, if C is set to a value of 0.9, the process will terminate as soon as the inlet force is less than 90% of the total measured force. At this point, the controller no longer enables the actuator to move the adjustable bed support and the column is packed.

The rate of increase in the total measured force 300 is a function of the media type. For example, in a rigid media, the increase as the media nears compression is drastic. However, in softer media, the change is much less obvious. To accommodate these different media types, the sensitivity of the control system can be varied, as a function of the media type. The noise rejection of the system can be increased when packing rigid media, since the increase in force is clearly obvious. However, in softer media, the noise rejection cannot be as great, due to the lack of an obvious increase in the total force.

In addition to this preferred method of packing a column using constant velocity, there are several other alternative methods that can be used as well. For example, in one alternate method, the termination point can be determined solely by monitoring the total measured force, as shown in FIG. 3. This can be done by either comparing the total measured force to an absolute value, or by monitoring the slope (i.e. the derivative) of the line 300. Referring to FIG. 3, it is seen that the total measured force is approximately linear with respect to time until the packing process is completed. At that point 320, the slope of line 300 changes significantly. Thus, the derivative of the line would have a change in value or a discontinuity at this point in time. By evaluating the derivative of this line, the controller can determine this point, without the need for a predetermined terminal force, or using a predetermined ratio between the inlet force and the total measured force. This method is most effective when used with rigid media, since the media compression forces associated with this media type are easily observable.

Alternatively, instead of comparing the inlet force to the total measured force as shown in Decision Box 450, the controller can evaluate the force associated solely with the media compression. Referring to FIG. 3, this force can be expressed as line 300, less line 310. This force can then be evaluated according to any of the methods described above, i.e. as compared to the total measured force, as compared to a predetermined value, or by monitoring its derivative.

Figure 5:
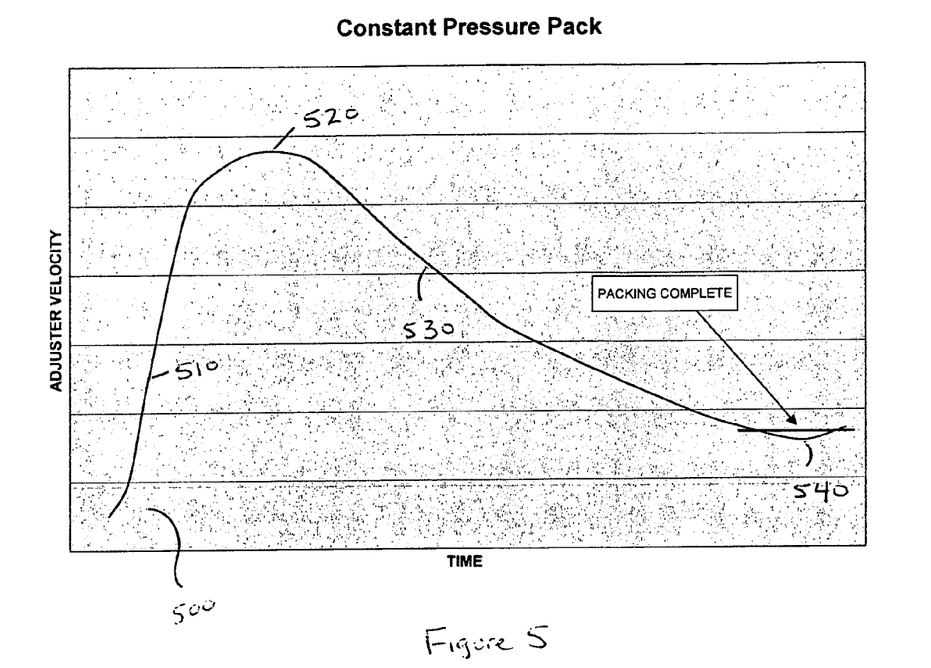
FIG. 5 represents a graph illustrating the velocity of the adjuster during a constant pressure packing process in accordance with the present invention.
Figure 6:
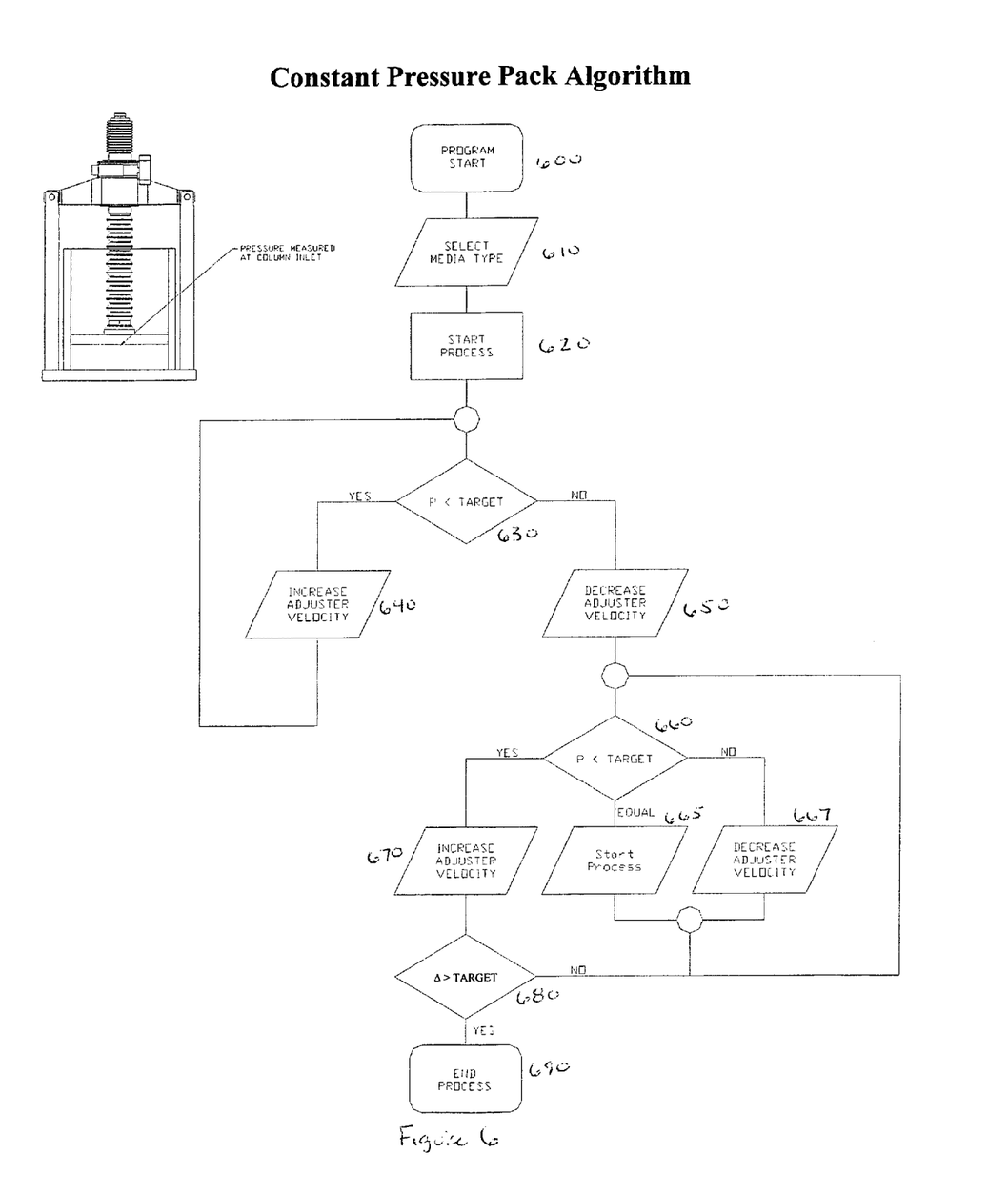
FIG. 6 represents a flowchart illustrating the steps performed during a constant pressure packing process in accordance with the present invention.

Alternatively, a chromatography column can be automatically packed where, instead of moving the adjuster at a constant velocity as described above, the pressure measured at the column inlet is held constant. A flowchart showing one embodiment of a constant velocity packing process algorithm is illustrated in FIG. 6. Boxes 600, 610 and 620 are analogous to Boxes 400, 410 and 420 in the constant velocity algorithm, in that it is during these steps that the controller defines the constant parameters that are to be used by the algorithm, based on the media type. In Decision Box 630, the algorithm increases the velocity of the adjuster, preferably an adjustable bed support, until it reaches the target pressure value. As long as the measured pressure is less than the targeted value, the controller will continue to increase the velocity of the adjustable bed support, as shown in Box 640. FIG. 5 represents a graph illustrating the velocity of the adjustable bed support as a function of time during a constant pressure packing process. Line 500 represents the velocity of the adjuster as a function of time. Line segment 510 corresponds to the Box 640 and Decision Box 630 in FIG. 6, in that this is the portion of the time in which the velocity of the adjustable bed support is increased. Once the desired pressure has been reached, shown as point 520 in FIG. 5, the algorithm continues with Box 650, in which the controller reduces the velocity of the adjustable bed support. The measured pressure is then compared with a target value in Decision Box 660. This target value is one of the parameters that is based on the media type. If the measured pressure is greater than the target value, the velocity of the adjustable bed support continues to be decreased by the controller in Box 667. This set of steps is performed repeatedly as the adjuster velocity decreases as shown on line segment 530 of FIG. 5. The velocity must be continuously decreased because the media bed is growing in height and therefore is creating increasing resistance to flow. This will continue until the entire bed has been formed. Once the entire bed is formed, the pressure and velocity will reach a steady state value for a short period, as shown at point 540 in FIG. 5. At this point, the inlet pressure will equal the target value. At this point, the algorithm proceeds to Box 665, where the current velocity of the adjustable bed support is measured and stored to be used as a reference later. After this steady state has been reached, there will no longer be sufficient fluid left within the media to maintain the desired hydraulic pressure. Thus, the velocity will need to be increased to maintain the desired pressure. This is illustrated in Box 670, which is executed when the hydraulic pressure becomes less than the targeted value. The velocity is increased and the new velocity is compared to the reference velocity which was stored in Box 665. If the new velocity is greater than that reference by a predetermined amount, the algorithm is completed and the process ends in Box 690. If the velocity is not yet greater than the reference value by that predetermined amount, the algorithm returns to Decision Box 660 and the loop repeats until the process is completed.

There may be situations in which the measured inlet pressure transitions from being less than the target value to more than the target value without ever being measured at exactly the target value. In other words, Box 665 is never executed. In this case, Box 670, in addition to increasing the adjuster velocity, would also check if a reference value has already been stored. If one has not been stored, the algorithm will measure and store the current velocity in the same manner as was described in reference to Box 665 above.

The measurements used in both flowcharts are preferably calculated by the controller, which first reads the actual values from the appropriate measuring device and then processes that result using an algorithm, such as PID, such that minor fluctuations are filtered from the analysis. The values used by the flowcharts are therefore less susceptible to noise and erroneous readings.

In a third embodiment of the present invention, the column is packed following specific parameters entered into the system. For example, there may be situations where the use of a computerized control loop to determine the optimal packing point is not advantageous. For example, the user may wish to run multiple tests in which the column is packed exactly the same each time. The use of the aforementioned algorithms yields optimal results, but cannot be guaranteed to pack identical columns in the identical manner to the identical height due to small algorithmic and measurement variations. For example, two identical columns packed using the constant velocity algorithm described above may terminate at slightly different column heights.

Thus, the present invention comprises a third embodiment, which is designed to repeat the identical packing process for any number of columns. In this embodiment, various parameters, such as, but not limited to, media type, adjuster velocity and terminal column height, are made known to the system, such as via menus or keypad entry. The system then, in the preferred implementation, performs a constant velocity packing process, utilizing the supplied desired velocity. The process is completed when the column height matches the terminal column height that was inputted to the system. It is envisioned that the velocity that is used would be a function of the media type, as in the previous embodiments. The optimal terminal column height can be determined empirically. For example, several columns can be packed using the second embodiment of the present invention, in which the system determines the optimal column height using either the constant velocity or constant pressure packing algorithm. The terminal column heights from each of these packing processes can then be used to determine an optimal terminal column height. This optimal value, along with the media specific velocity or pressure, are then made known to the system. Then, in accordance with the third embodiment of the present invention, the column is packed.

What is claimed is:

1. A method of packing a media bed of an unknown media slurry, wherein said unknown media is from a set of known media types, in a chromatography column having an adjuster adapted to compress said media and means for measuring the force on said adjuster, said method comprising:
   actuating said adjuster to compress said media to a first column height;
   measuring the force on said adjuster at said first column height;
   calculating an index value based on said force measured at said first column height;
   determining said unknown media type by comparing said index value to the index value of each of said known media types;
   selecting packing parameters based on said determined media type; and
   packing said column based on said selected packing parameters.

2. The method of claim 1, further comprising:
   actuating said adjuster to compress said media to a second column height;
   measuring the force on said adjuster at said second column height; and
   wherein said step of calculating an index value comprises computing an index value by comparing the difference between said force at said first column height and said force at said second column height to the difference between said first column height and said second column height.

3. The method of claim 1, wherein said packing step comprises:
   actuating said adjuster to compress said bed;
   determining said force on said adjuster; and
   ceasing movement of said adjuster when said force reaches a predetermined level.

4. The method of claim 1, wherein said packing step comprises:
   actuating said adjuster to compress said bed;
   determining said force on said adjuster;
   calculating the time derivative of said force; and
   ceasing movement of said adjuster when said time derivative of said force reaches a predetermined level.

5. The method of claim 1, wherein said force on said adjuster comprises a compression force from said media and a hydraulic force from a fluid flowing through said column, and said chromatography column comprises means for measuring the compression force on said adjuster, and said packing step comprises:
   actuating said adjuster to compress said bed;
   determining said compression force on said adjuster; and
   ceasing movement of said adjuster when said compression force reaches a predetermined level.

6. The method of claim 1, wherein said force on said adjuster comprises a compression force from said media and a hydraulic force from a fluid flowing through said column, and said chromatography column comprises means for measuring the compression force on said adjuster, and said packing step comprises:
   actuating said adjuster to compress said bed;
   determining said compression force on said adjuster;
   calculating the time derivative of said compression force; and
   ceasing movement of said adjuster when said time derivative of said compression force reaches a predetermined level.

7. The method of claim 1, wherein said force on said adjuster comprises a compression force from said media and a hydraulic force from a fluid flowing through said column, and said chromatography column comprises means for measuring the compression force on said adjuster, and said packing step comprises:
   actuating said adjuster to compress said bed;
   determining said compression force and said force on said adjuster;
   calculating the ratio of said compression force to said force; and
   ceasing movement of said adjuster when said ratio reaches a predetermined level.

8. The method of claim 1, wherein said force on said adjuster comprises a compression force from said media and a hydraulic force from a fluid flowing through said column, and said chromatography column comprises means for measuring the hydraulic force on said adjuster, and said packing step comprises:
   actuating said adjuster to compress said bed;
   determining said hydraulic force and said force on said adjuster;
   calculating the ratio of said hydraulic force to said force; and
   ceasing movement of said adjuster when said ratio reaches a predetermined level.

9. The method of claim 1, wherein said force on said adjuster comprises a compression force from said media and a hydraulic force from a fluid flowing through said column, and said chromatography column comprises means for measuring the hydraulic force on said adjuster, and said packing step comprising the sequential steps of:
   actuating said adjuster at such a velocity such that said hydraulic pressure reaches a predetermined level;
   decreasing the velocity of said adjuster to maintain said hydraulic pressure at said predetermined level;
   increasing the velocity of said adjuster to maintain said hydraulic pressure at said predetermined level; and
   ceasing movement of said adjuster when its current velocity is greater than its velocity at the transition between said decreasing and increasing steps by a predetermined amount.

10. The method of claim 1, wherein said chromatography column comprises means for determining the position of said adjuster within said column, and said packing step comprises:
actuating the adjuster at a predetermined velocity; and
ceasing movement of said adjuster when said adjuster reaches a predetermined position within said column.

* * * * *